United States Patent [19]

Rydell

[11] Patent Number: 4,905,691
[45] Date of Patent: Mar. 6, 1990

[54] POLYPECTOME SNARE WITH BIPOLAR ELECTRODES

[75] Inventor: Mark A. Rydell, Golden Valley, Minn.

[73] Assignee: Everest Medical Corporation, Brooklyn Center, Minn.

[21] Appl. No.: 344,073

[22] Filed: Apr. 17, 1989

[51] Int. Cl.$^4$ .............................................. A61B 17/39
[52] U.S. Cl. ........................................ 606/47; 606/48
[58] Field of Search ...................... 128/303.14, 303.15, 128/303.16, 303.17, 320

[56] References Cited

U.S. PATENT DOCUMENTS

| | | | |
|---|---|---|---|
| 4,311,143 | 1/1982 | Komiya | 128/303.15 |
| 4,493,320 | 1/1985 | Treat | 128/303.15 |

FOREIGN PATENT DOCUMENTS

| | | | |
|---|---|---|---|
| 2514501 | 10/1976 | Fed. Rep. of Germany | 128/303.17 |
| 2275226 | 1/1976 | France | 128/303.17 |

Primary Examiner—Lee S. Cohen
Attorney, Agent, or Firm—Haugen and Nikolai

[57] ABSTRACT

A polypectome snare whose loop comprises a pair of electrodes mechanically joined but electrically insulated from one another at their distal ends and adapted to be energized by a source of RF voltage for excising polyps on the inside of a body cavity is described. The polypectome snare is designed to be used with an endoscope and includes two concentric flexible plastic tubes each having proximal and distal ends and a lumen running the length thereof. At the proximal end is a hand grip which is secured to the wires leading to the bipolar electrodes with one of the wires passing through the lumen of the outermost tube and the other wire extending through the lumen of the inner tube. In this fashion, the wires remain insulated from one another over the length of the instrument and due to this same arrangement, the conductors comprising the bipolar electrodes cannot become twisted at the distal end of the implement to thereby create a short which would render the snare inoperative.

7 Claims, 1 Drawing Sheet

U.S. Patent   Mar. 6, 1990   4,905,691
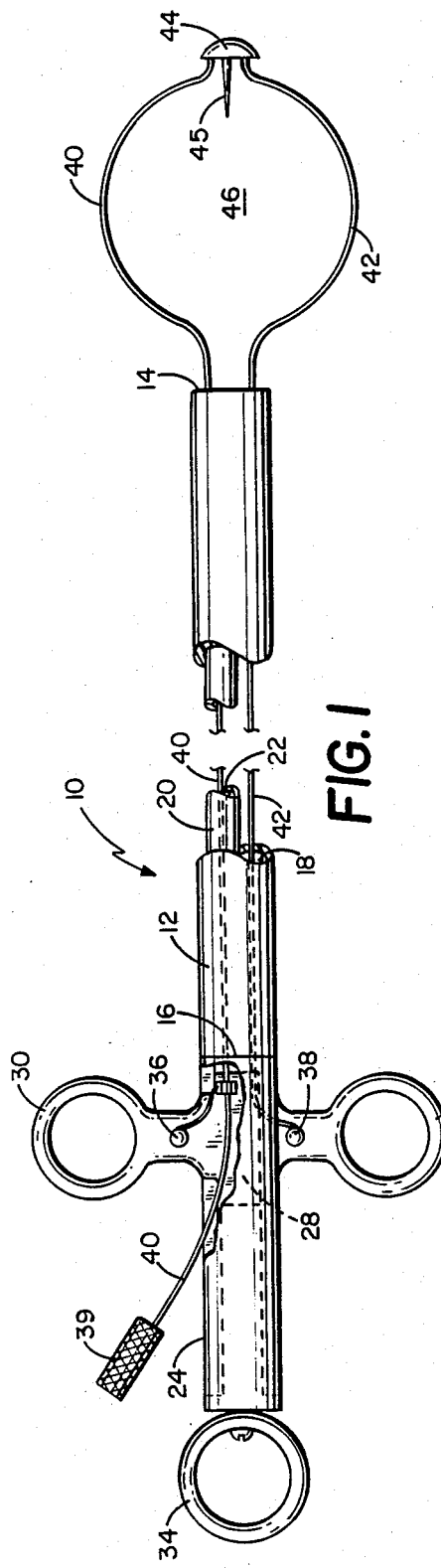
FIG. 1
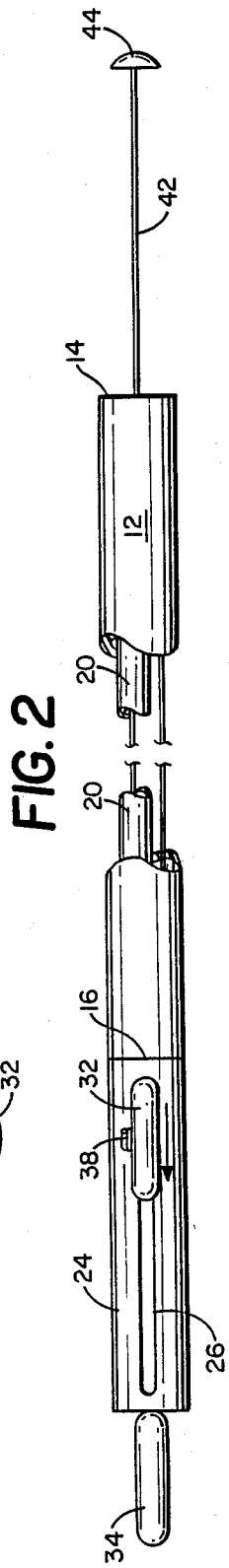
FIG. 2
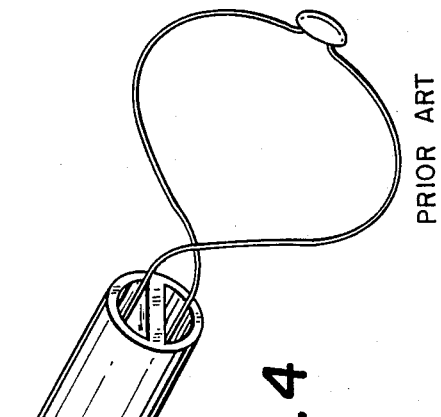
FIG. 3
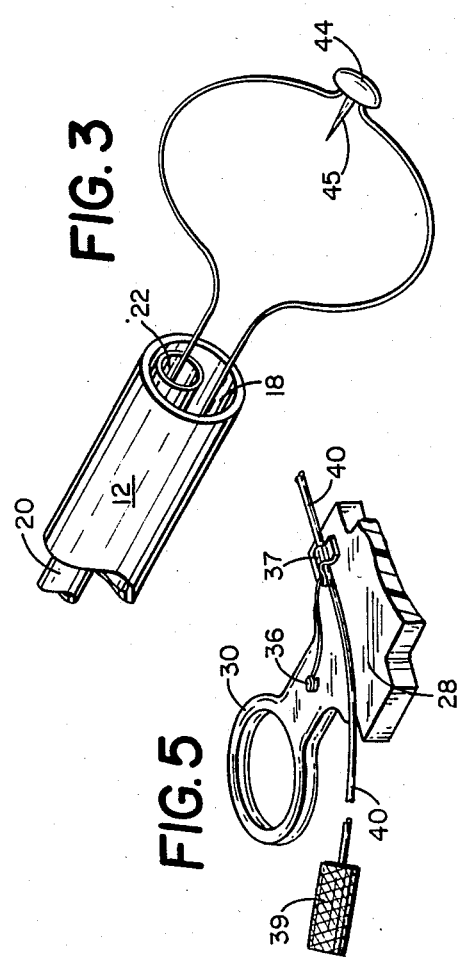
FIG. 4 PRIOR ART
FIG. 5

POLYPECTOME SNARE WITH BIPOLAR ELECTRODES

BACKGROUND OF THE INVENTION

1. Field of the Invention

This invention relates generally to electrosurgical apparatus, and more particularly to an improved polypectome snare for use in excising polyps from an internal body cavity.

2. Discussion of the Prior Art

In U.S. Pat. No. 4,311,143 to Komiya, there is described the construction of a bipolar electrosurgical polypectome snare which comprises an elongated, flexible plastic tube whose outside diameter is sufficiently small to permit it to pass through the lumen of an endoscope and affixed to the distal end of the tube is a first electrode in the form of an annular metallic cap. The second electrode comprises a wire loop which can be extended and retracted relative to the distal end of the tubular body. When inserted through the lumen of an endoscope, it can be made to loop around the polyp to be excised and then by manipulating a hand grip member, the loop can be drawn tight about the neck of the polyp as RF energy is applied between the annular cap and the wire loop. The tissue comprising the polyp completes the circuit between the two electrodes and with sufficient power applied, the stem of the polyp will eventually be cut through.

The device describe in the Komiya Pat. No. 4,311,143 suffers from a number of defects. First of all, because of the disparity in surface area between the small annular cap electrode on the end of the tubular and the larger wire loop, the metallic cap becomes the active electrode and the wire loop merely serves to draw the tissue against the cap. Because of its shape, it tends to desiccate the tissue until the tissue impedance becomes sufficiently high for the wire loop to become the active electrode and effect cutting. This necessarily tends to slow down the cutting action and exposes surrounding healthy tissue to elevated temperatures for a prolonged period.

The Treat U.S. Pat. No. 4,493,320 describes a polypectome snare having a bi-lumen tube dimensioned to fit through an endoscope and where a pair of wires are routed through each of the lumens and extend beyond the distal end thereof where they are joined with an insulating tip member. Thus, portions of the wires themselves become the active bipolar pair.

A problem exists with this construction, however, in that it frequently becomes necessary to rotate the loop at least 90° in those cases where the loop of the snare exits the distal end of the tubular portion in the wrong plane to engage the polyp to be excised. When an effort is made to rotate the plane of the loop by twisting one or the other of the two wires at its distal end, there is a tendency for the loop to twist at its base and thereby create a short circuit condition.

SUMMARY OF THE INVENTION

The present invention provides a polypectome snare in which the foregoing deficiency of the apparatus of the Komiya and Treat Patents are obviated. Rather than having the loop or snare as a first electrode and a toroidal end cap as a second electrode as in Komiya, in the present invention, the conductive loop or snare is effectively divided so that one-half thereof comprises a first electrode and the other half a second electrode as in the Treat patent. As such, the area of tissue contact between the two electrodes is the same. One does not dominate and merely cause heating rather than RF cutting. However, the present invention solves the twisting problem encountered with a snare like in Treat.

To achieve the foregoing advantages, the polypectome snare comprising the preferred embodiment consists of a first elongated flexible plastic tube having a proximal end, a distal end and a lumen extending between the two. Concentrically disposed and loosely fitting within the lumen of the first tube is a second elongated, flexible, plastic tube of generally equal length. A first electrical conductor having an exposed metal distal portion extends through the lumen of the first tube from a terminal point at the proximal end and a second, identical electrical conductor extends through the lumen of the second tube. As such, the two remain electrically isolated from one another within the confines of the first tube. An insulating spacer is used to couple the distal ends of the first and second conductors together to thereby form a loop, but with an electrical insulator between the two segments thereof. Connected to the proximal end of the first and second plastic tubes is a hand grip having a slide portion to which one of the first or second conductors is fixedly attached. The other of the two wires passes through a conductive slip-ring mounted on the slide and exits the slide so as to be accessible to the physician. It is provided with a knurled knob on its proximal end whereby the wire in question can be torqued to thereby twist the plane of the snare's loop when necessary. By manipulating the hand grip, the loop can be retracted or extended relative to the distal end of the tubes through which the conductors pass. When the proximally located wire terminals are connected to a RF generator and the snare is looped around the stem of a polyp to be removed, an arc is created through the tissue as the snare is tightened about the stem of the polyp. This arc rapidly cuts through the stem, severing the polyp from surrounding healthy tissue without undue heating of that surrounding tissue.

A significant advantage attendant to the construction of the preferred embodiment when compared to the device of the Treat patent is that the two conductors are free to float within the respective lumens of the first and second tubes. As such, rotation of the proximal end of one of the two wires in an attempt to rotate the loop to gain purchase to the polyp does not result in twisting of the wires together at the base of the loop to create a short circuit at that point and rendering the loop electrically inactive. Instead, the wires remain physically spaced from one another upon limited twisting and manipulation of the snare device.

DESCRIPTION OF THE DRAWINGS

Further features and advantages of the invention will become apparent to those skilled in the art from the following detailed description of a preferred embodiment, especially when considered in conjunction with the accompanying drawings in which like numerals in the several views refer to corresponding parts.

FIG. 1 is a plan view of the polypectome snare constructed in accordance with the present invention;

FIG. 2 is a side elevation of the apparatus of FIG. 1;

FIG. 3 is a partial perspective view of the distal end portion of the polypectome snare of FIG. 1;

FIG. 4 shows the distal end portion of an alternative and inferior way of constructing a polypectome snare in accordance with the prior art; and FIG. 5 is a partial view showing the slip ring arrangement of FIG. 1 in greater detail.

DESCRIPTION OF THE PREFERRED EMBODIMENT

Referring to FIG. 1, there is indicated generally by numeral 10 the radio frequency polypectome snare in accordance with the present invention. It is seen to include a first, outer tubular member 12 preferably formed from a flexible plastic material whose outside diameter is sufficiently small to permit the instrument to be passed through the lumen of an endoscope (not shown). The tubular member 12 has a distal end 14 and a proximal end 16. A lumen 18 extends the full length thereof and disposed within the lumen 18 is a second elongated flexible plastic tubular member 20 which is generally coextensive in length with the outer tube 12. The second or inner tube 20 has a lumen identified by numeral 22 (see FIG. 3).

Affixed to the proximal end 16 of the tubes 12 and 20 is a hand grip assembly including a molded plastic housing member 24 having a longitudinal slot 26 formed on the lateral sides thereof. Fitted into the housing 24 is a slide member 28 which is adapted to ride in a groove formed in the housing 24. Integrally molded with the slide member 28 and extending through the longitudinal slots 26 on opposed sides of the housing are finger grip members 30 and 32, here shown as being annular in shape for receiving the forefinger and index finger of one hand. A further ring 34 is affixed to the proximal end of the housing 24 and is intended to receive the user's thumb therein.

The grip members 30 and 32 further include a pair of terminals 36 and 38 to which one of the first or second electrical conductors 40 and 42 attach.

The other of the two wires fits through a conductive slip ring 37 affixed to the slide member 28 and movable therewith. As seen in the distal view of FIG. 4, the slip ring member 37 is then connected to the remaining one of the terminals 36. The output of the RF generator (not shown) is also connected by suitable leads to these two terminals. The conductor 40 extends through the lumen 22 of the inner tube 20 and beyond the distal end 14 thereof. Likewise, the conductor 42 is fed through the lumen 18 of the outer tube 12 and also extends beyond the distal end 14. At least the distal end portions of the wires 40 and 42 are bare metal and are mechanically coupled but electrically insulated from one another by means of a ceramic button 44. The conductors are preferably stainless steel and are preformed to exhibit a memory property at their distal end so that when unconstrained they will cooperate to form an open loop. It is also contemplated that a pin or spike 45 be made to project from the button 44 as shown to retain the polyp tissue once it has been cut loose. The proximal end of wire 40 is seen to pass through the slip ring member 37 and affixed to the end thereof is a knurled plastic knob 39 to facilitate the rotation of wire 40 within its lumen. The slip ring 37 allows the electrical current from the RF generator to be impressed on the wire 40 while still permitting the loop to be closed by retracting the grip.

In FIGS. 1 and 2, the slide 28 is illustrated as being in its most forward or distal position relative to the slot 26. As such, the loop 46 defined by the end portions of the conductors 40 and 42 extends outward beyond the distal end 14 of the tubes 12 and 20. It will be appreciated, however, that when the slide 28 is pulled rearward, i.e., in the proximal direction, the wires 40 and 42 will be retracted into their respective tubes 12 and 20 until the insulating button 44 abuts the distal end of the inner tube 20.

In use, a radio frequency generator will have its output connected by a cable to the terminals 36 and 38 of the polypectome snare. The terminal 38 is connected to the slip ring 37. In that the wires 40 and 42 are fully contained over most of their length within separate plastic insulating tubes, they remain shielded against short circuiting. With the slide in its most proximal position, the distal end portions of conductors 40 and 42 will be retracted into the lumen of its respective tube. In this configuration, the snare assembly 10 can readily be inserted through an endoscope into the body organ from which the polyps are to be removed. By pushing the slide member 28 in the distal direction, the wires 40 and 42 comprising the bipolar electrodes will exit the distal end 14 of the tubes and, because of the memory property of the wires employed, will spring into an open loop as best illustrated in FIGS. 1 and 3. By manipulating the knob 39 on wire 40 at the proximal end of the endoscope, the loop 46 can be made to rotate into alignment with the polyp and made to surround the stem thereof. If the wire 40 alone is found to be too fine to adequately transfer torque from knob 39 to the loop 46, the wire may be provided with a nylon jacket (not shown) to increase that property. Now, when the RF power source is energized and the slide member 28 is retracted in the proximal direction to again close the loop, the electrodes 40 and 42 will encircle the stem of the polyp to the point where an arc discharge is created, thereby rapidly severing the stem tissue. The end cap 44 is designed to pull free of the ends of the wires 40 and 42 when a reasonable force is applied. Thus, if the impedance of the tissue should become so high that cutting ceases, the tool can readily be pulled free.

An important feature of the preferred embodiment is that the snare 10 may be rotated several complete revolutions while maintaining the wire loop stationary and, in doing so, will not result in a crossing and shorting of the electrodes in the fashion depicted by FIG. 4 which is taken from the prior art Treat Pat. No. 4,493,320. Instead, when the loop is torqued by rotating the knob 39 on conductor 40, wire 42 is free to move around within the annular space surrounding the inner tube 20 as is best seen in FIG. 3.

The polypectome snare of the present invention can be fabricated from a variety of available materials. For example, various medical grade plastics may be employed in molding the hand grip portion with polycarbonate being preferred. The tubes 12 and 20 may be extruded polyethylene, polyurethane, polypropylene or Teflon ®, with Teflon being preferred. The conductors 40 and 42 are preferably formed from stainless steel, although other materials may be used as well and because of the manner in which they are isolated from one another in traversing the length of the tubes, need not themselves be coated with an insulator.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An electrosurgical polypectome snare comprising:
   (a) a first elongated flexible plastic tube having a proximal end, a distal end and a lumen extending between said proximal end and said distal end of said first tube;
   (b) a second elongated, flexible plastic tube having a proximal end, a distal end and a lumen extending between said proximal end and said distal end of said second tube, said second tube being disposed within said lumen of said first tube;
   (c) a first electrical conductor having a proximal end and distal end, said first conductor extending through said lumen of said first tube;
   (d) a second electrical conductor having a proximal end and a distal end, said second conductor extending through said lumen of said second tube;
   (e) insulating spacer means coupling said first and second electrical conductors together at said distal ends thereof to form a loop;
   (f) manually operable means joined to said proximal ends of said first and second tubes for imparting longitudinal translational motion to at least one of said first and second conductors to vary the size of said loop extending beyond said distal end of said first and second tubes;
   (g) terminal means at the proximal end of said conductors for connecting said conductors to a source of radio frequency voltage; and
   (h) means disposed at said proximal end of one of said first and second conductors for imparting rotation to said one of said first and second conductors.

2. The polypectome snare as in claim 1 wherein the outer diameter of said first tube is sufficiently small to pass through an endoscope with the outer diameter of said second tube allowing said first conductor to move freely within said lumen of said first tube.

3. The polypectome snare as in claim 1 wherein said first and second conductors have portions adapted to contact tissue to be cut which are of generally equal size.

4. The polypectome snare as in claim 3 wherein the distal portions of said first and second conductors are preformed to spring out into an open loop when extended outwardly from said lumens of said first and second tubes.

5. The polypectome snare as in claim 1 further including means for preventing said first and second conductors from twisting about one another when said one of said first and second conductors is rotated by said means for imparting rotation about its own longitudinal axis when said loop is held fixed.

6. The polypectome snare as in claim 1 wherein said terminal means includes a slip ring disposed about one of said first and second conductors.

7. The polypectome snare as in claim 6 wherein said one of said first and second conductors passing through said slip ring can be rotated by said means for imparting rotation and translated by said manually operable means while remaining in electrical contact with said slip ring.

* * * * *